United States Patent [19]

Goeth et al.

[11] Patent Number: 5,178,857

[45] Date of Patent: Jan. 12, 1993

[54] PHARMACEUTICAL COMPOSITIONS AND THEIR USE IN THE TREATMENT OF PARASITOSES

[75] Inventors: Hanns Goeth, Biberach; Werner Frank, Filderstadt; Ingeborg Renner, Stuttgart, all of Fed. Rep. of Germany

[73] Assignee: Boehringer Ingelheim International GmbH, Ingelheim am Rhein, Fed. Rep. of Germany

[21] Appl. No.: 501,812

[22] Filed: Mar. 30, 1990

[30] Foreign Application Priority Data

Apr. 1, 1989 [DE] Fed. Rep. of Germany ....... 3910568

[51] Int. Cl.⁵ .............................................. A61K 37/66
[52] U.S. Cl. ...................... 424/85.5; 514/2; 514/12; 514/21
[58] Field of Search ................. 424/85.5; 514/2, 12, 514/21

[56] References Cited

U.S. PATENT DOCUMENTS 4,510,144  4/1985  Hadden et al. ................... 514/257

OTHER PUBLICATIONS

Campbell, W., et al, *J. Parasit.*, 61(5):844-852 (1975).
Eckert, J., et al., *Schweiz. med. Wschr.*, 108:1104-1112 (1978).
O'Malley, J., *Met. Enzym.* 78:540-545 (1981).
Biedermann, H., et al., *Aktuel. Probl. Chir. Orthop.* 23:98-99 (1982).
Junge, U., et al., *Aktuel. Probl. Chir. Orthop.* 23:100-103 (1982).
Van den Bossche, H., *Adv. Pharmac. Chemother.* 19:66-128 (1982).
Levin, S., *Israel J. Med. Sci.*, 19:955-958 (1983).
Kiderlen, A., et al., *Eur. J. Immunol.*, 14:964:967 (1984).
Mauël, J., et al., *Eur. J. Immunol.*, 17:203-208 (1987).
Suzuki, Y., et al., *Science*, 240:516-518 (1988).
Reed, S., *J. Immunol.*, 140:4342-4347 (1988).
Suzuki, Y., et al., *Chem. Abstracts*, 108:203081y (1988).
Kiderlen, A. F. et al., Interdisciplinary Conference on Primary Health Care in the Tropics, Tropical Diseases and Zoonoses, Apr. 13-15, 1987, WHO Genf.
Clark, I. A. et al., *The Journal of Immunology* 139 (10):3493-3496 (1987).
DeLoach, J. R. et al., *Res. Exp. Med.* 183:167-175 (1983).
Lee, D-Y., et al., *J. Lab. Clin. Med.* 114 (6):639-645 (1989).
Webster, Leslie T., Jr., *The Pharmacological Basis of Therapeutics*, 8th ed., Goodman and Gilman (eds.), pp. 954-977, Pergamon Press, New York, N.Y. (1990).
*Harrison's Principles of Internal Medicine*, 11th ed., E. Braunwald et al. (eds.), p. 1316, McGraw-Hill Book Co. New York, N.Y. (1987).
Worthington Enzyme Manual, Decker, L.A. (ed.), pp. 88-89, Worthington Biochemical Corp., Freehold, N.J. (1977).
Swinyard, E. A., Parasiticides, in *Pharmaceutical Sciences*, 17th ed., Gennaro, A. R. (ed.), pp. 1234-1239, Mack Publishing Co., Easton, Pa. (1985).
*Martindale The Extra Pharmacopoeia*, 29th ed., Reynolds, J. E. F. et al. (eds.), The Pharmaceutical Press, London, (1989).

Primary Examiner—Merrell C. Cashion, Jr.
Assistant Examiner—Andrew G. Rozycki
Attorney, Agent, or Firm—Sterne, Kessler, Goldstein & Fox

[57] ABSTRACT

The present invention relates to pharmaceutical combinations containing IFNγ and at least one anthelminthic, and the use thereof for treating parasitoses in mammals or in humans.

8 Claims, 5 Drawing Sheets

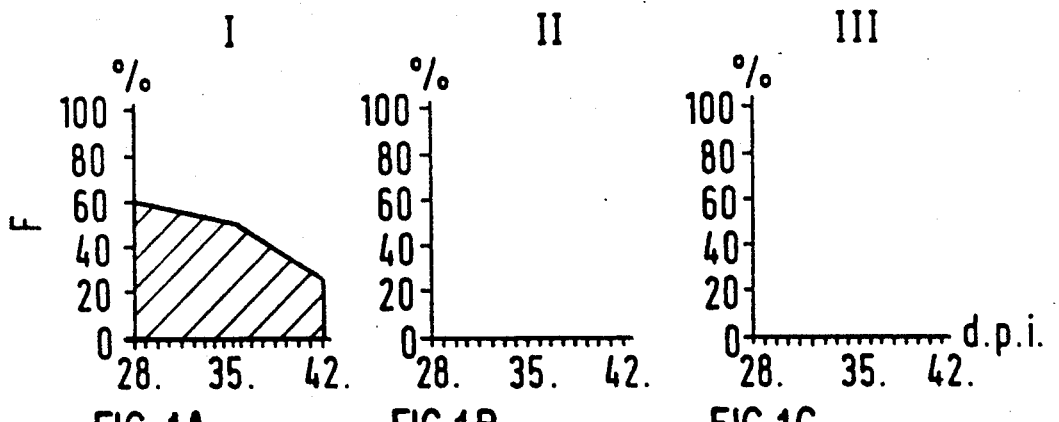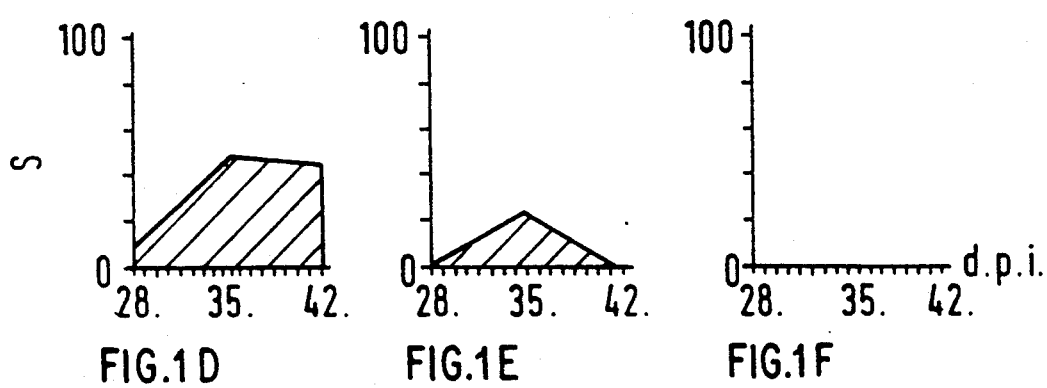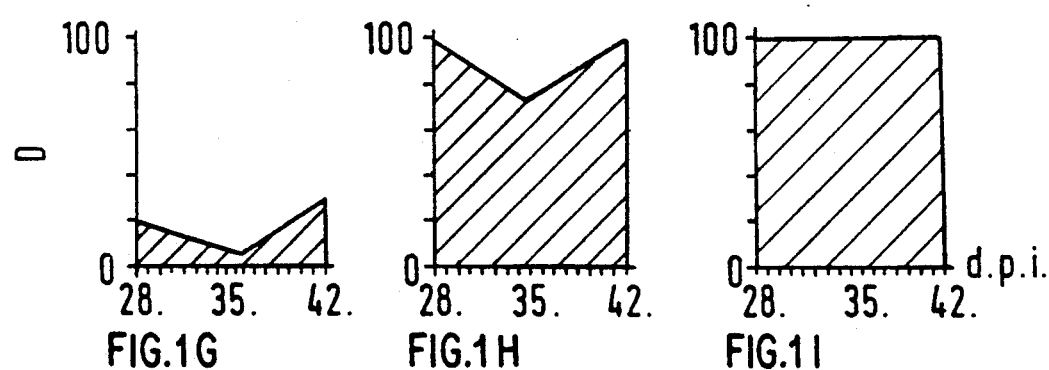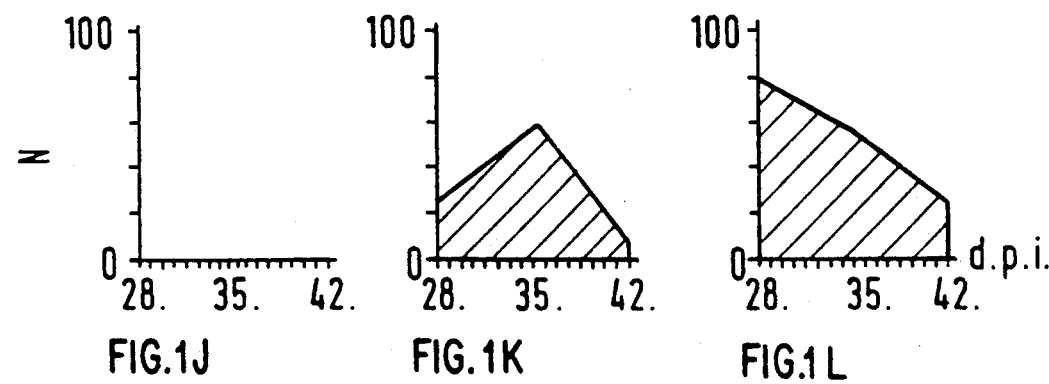

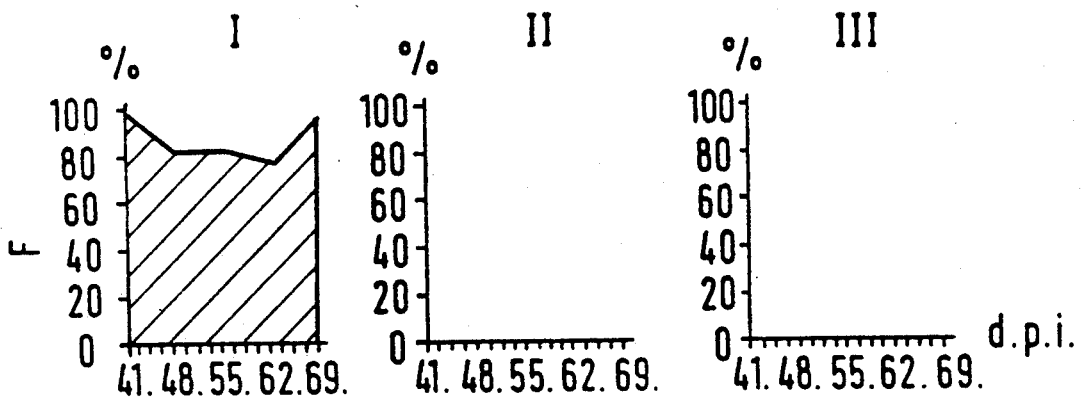
FIG. 4A  FIG. 4B  FIG. 4C
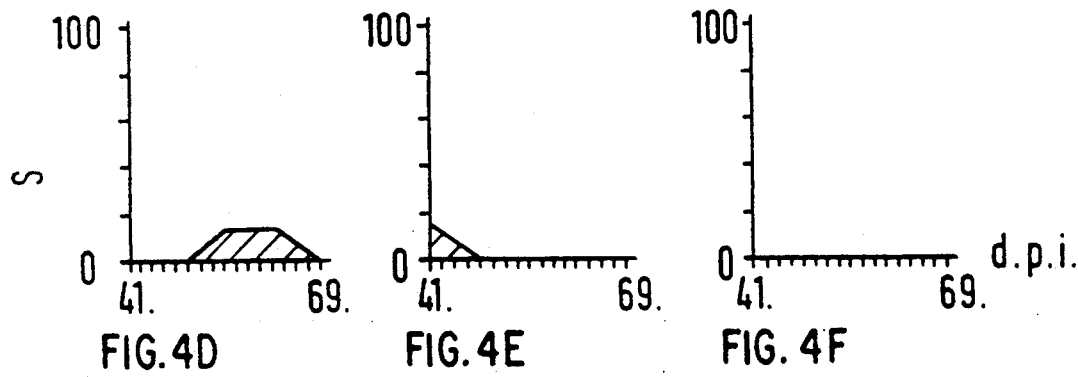
FIG. 4D  FIG. 4E  FIG. 4F
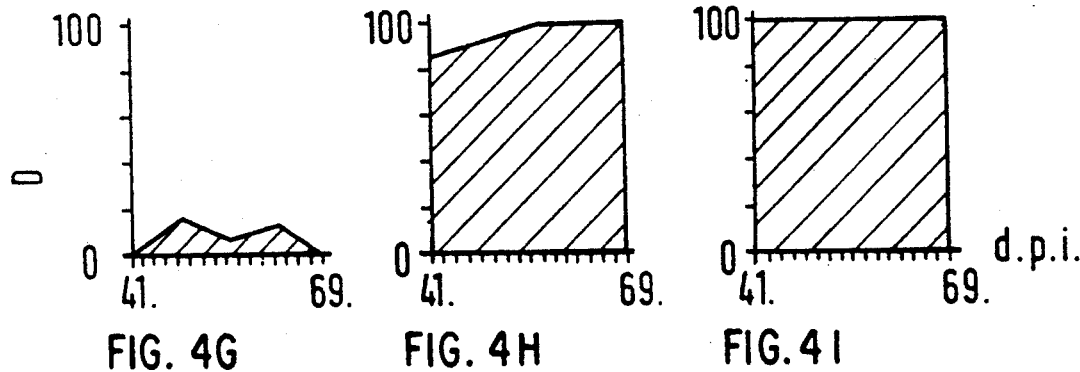
FIG. 4G  FIG. 4H  FIG. 4I
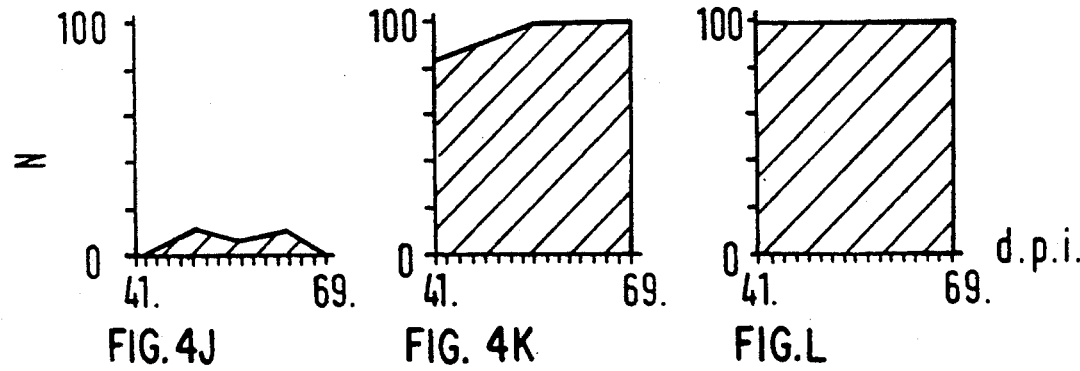
FIG. 4J  FIG. 4K  FIG. L

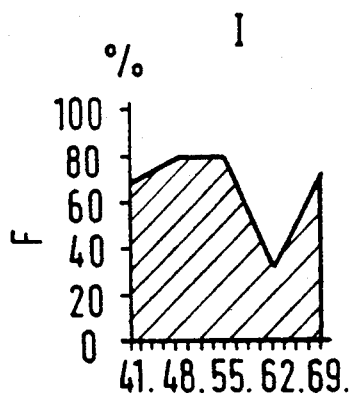
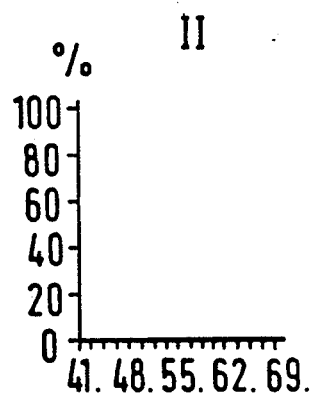
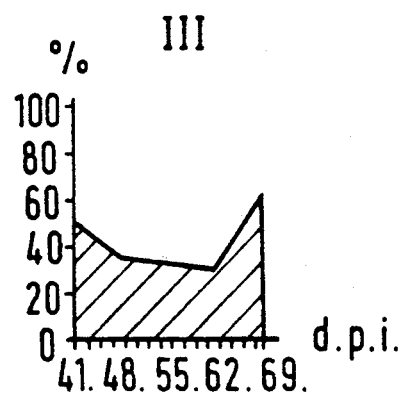
FIG. 6A  FIG. 6B  FIG. 6C
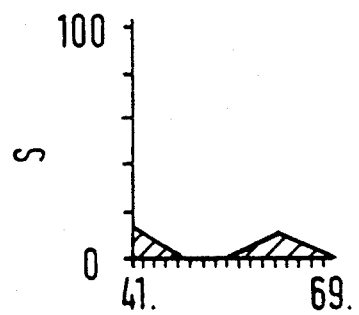
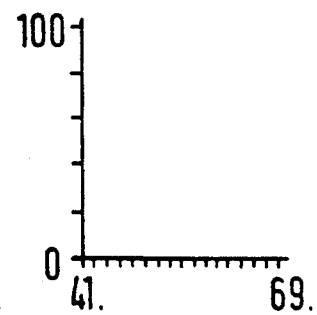
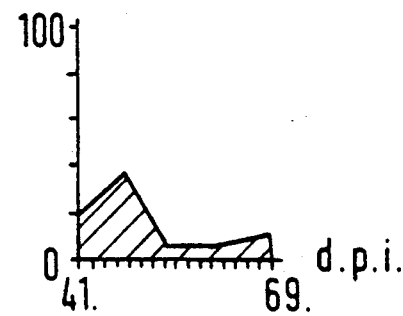
FIG. 6D  FIG. 6E  FIG. 6F
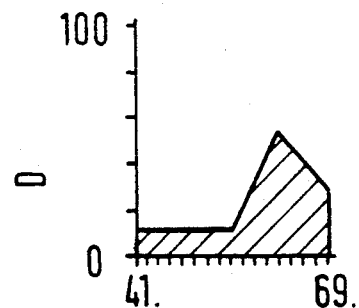
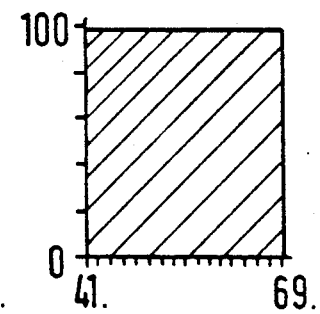
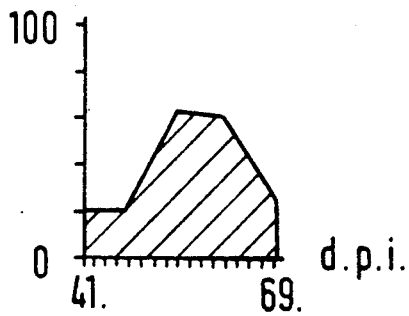
FIG. 6G  FIG. 6H  FIG. 6I
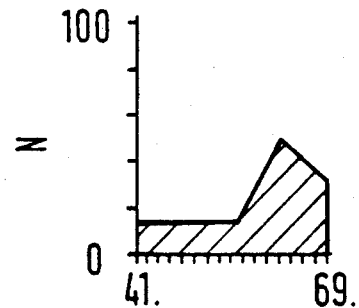
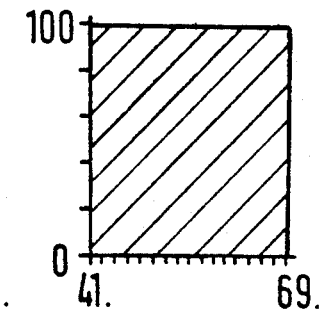
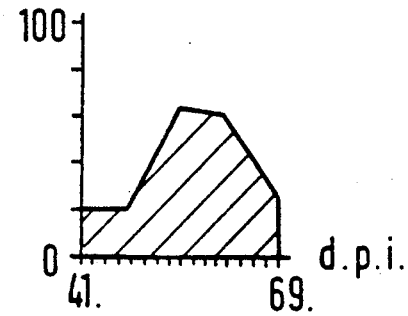
FIG. 6J  FIG. 6K  FIG. 6L

PHARMACEUTICAL COMPOSITIONS AND THEIR USE IN THE TREATMENT OF PARASITOSES

FIELD OF THE INVENTION

The present invention relates to pharmaceutical compositions comprising an active substance combination of interferon-gamma (IFNγ) and at least one anthelminthic, and the use thereof in treating parasitoses in mammals.

The diseases to be treated with the drug combinations according to the invention include the infections caused by an attack by endoparasites, particularly of the class Cestodes, preferably of the order Cycloohyllidea, more particularly the genus Echinococcus. The drug combinations according to the invention are used, for example, to treat infections caused by the species *Echinococcus multilocularis*.

BACKGROUND OF THE INVENTION

Alveolar echinococcosis in particular can be regarded as the most dangerous parasitosis in humans in Central Europe (W., Frank in: Raumliche Persistenz und Diffusion von Krankheiten [W. Fricke, E. Hinz, Hrsg.], *Heidelb. Geoqr. Arb.* 83:86–113 (1987)).

This estimate is also supported by the World Health Organisation (WHO).

Infection with eggs of *Echinococcus* usually has catastrophic consequences for man when he is an accidental intermediate host.

The growth of the bladder worm in the case of *E. multilocularis* is slower in man than in the natural intermediate hosts, protoscolesces are frequently not even formed and central necrosis processes are typical. The disease often affects human health to the extent that it may result in death. According to 1. Drolshammer *et al.*, *Schweiz. med Wschr.* 103:1337–1386 (1973), mortality after an average period of 3.7 years is 52% after diagnosis and according to H.J. Schicker, Inaugural Diss. Med. Fak. University Tübingen (1976), about 20% survive for 5 years after diagnosis.

The pattern of the disease in man is furthermore extremely insidious. This is because diagnosis is made too late in the majority of cases, so that after the first symptoms of echinococcosis have appeared, with an attack on the liver, the chances of survival are very slight and only an unfavourable prognosis can be given.

In the time which has elapsed since echinococcosis was first described by Virchow in 1856 up to 1974, operative intervention was the only method of increasing the survival time or, in rare cases, effecting a cure. In 1974–75 the benzimidazoles were . then discovered for chemotherapy, including mebendazole (methyl [5-benzoyl-benzimidazol-2-carbamate]) (Campell, W.C. *et al.. J. Parasitol.* 61:844–852 (1975); Heath, D.D. *et al.. Parasitology* 70:273–285 (1975)).

Hitherto, mebendazole has generally been the only agent used in cases of alveolar echinococcosis. However, prognosis has remained unsatisfactory since this substance usually only has a parasitostatic effect in spite of being taken every day and its use is not entirely without problems. In addition, the mebendazole treatment does not totally cure the infection and once the treatment is discontinued the proliferative growth of the parasite stage (metacestode) may start up again. Then, in the last analysis, the only chance is an operation, again with an uncertain prognosis.

Benzimidazoles inhibit the synthesis of the microtubuli by binding to the dimeric component, tubulin (H. Van den Bossche et al.. In: Advances in pharmacology and chemotherapy. Vol. 19 [S. Garattini, A. Goldin, F. Hawkins, Kopin, Hrsg.], Academic Press New York, 67–128 (1982)). However, the binding affinity is not the same for each tubulin.

It is known from P.A. Friedmann & E.G. Platzer, *Biochem. Biophys. Acta* 630:271–278 (1980), that mebendazole binds 384 times more strongly to embryonic Ascaris suum-tubulin than to cattle brain tubulin, for example. Microtubuli are part of the cellular cytoskeleton and, in addition to their supporting function, also participate in the formation of the mitosis spindle and in intracellular transportation. Consequences of the benzimidazole activity may include cell division disorders, inhibition of the uptake of glucose (H. Van den Bossche, in Comparative biochemistry of parasites [H. Van den Bossche, Hrsg.], Academic Press, New York, 139–157 (1972)) with greater degradation of endogenous glycogen and inhibition of ATP synthesis (M.S. Rahman & C. Bryant, *Int. J. Parasitol.* 7:403–409 (1977)). The merely parasitostatic effect of mebendazole on *Echinococcus multilocularis* is based inter alia on the purely physical effect of the impaired diffusion of the active substance through the spongy cyst tissue, with a gelatinous lumen content, compared with *Echinococcus granulosus* (A. Dieckmann, Dissertation, Faculty II (Biol), University of Hohenheim (1987)).

The mebendazole therapy for human echinococcosis was started about 13 years ago. Today, it is still beset with many problems. For ethical reasons and on account of the high mortality rate it has not hitherto been possible to carry out any human experiments e.g. to discover the minimum effective concentration of mebendazole. Furthermore, there is no clear correlation between the dose and blood level. Further problems arise with the absence of reliable criteria for rapidly checking the success or failure of a therapy and insufficient knowledge of the nature and cause of side effects.

Nowadays, in general, a long term therapy of 40–50 mg/kg per day is the aim in inoperable or nonradically operated and recurring *Echinococcus multicularis* (R. Ammann et al.. in: Probleme der Echinokokkose unter Berücksichtigung parasitologischer und klinischer Aspekte [R. Bähr, Hrsg.], Huber Verlag Bern. Aktuel. Probl. Chir. OrthoD. 23:92–95 (1982); H. Biedermann ibidem. 98–99; U. Junge & P. Friedl, ibidem. 100–103; P. Kern & M. Dietrich, ibidem. 104–105).

Hitherto, it has been possible to achieve an improvement in the quality of life (H. Biedermann (1982), loc. cit.: U. Junge & P. Friedl, (1982), loc. cit.: P. Kern & M. Dietrich (1982), loc. cit.), a partial reduction in the Echinococcus AK titre (U. Junge & P. Friedl, (1982) loc. cit.), but no or only a slight regression in the intrahepatic tumour mass (R. Ammann et al. (1982), loc. cit.: P. Kern & M. Dietrich (1982), loc. cit.). R. Ammann et al.. (1982), loc. cit.. was able to detect active larval material in Echinococcus material removed by operating on 3 patients. This again appears to confirm the exclusively parasitostatic effect of mebendazole in Echinococcus infections.

IFNγ has hitherto been used mainly in virus, tumour or autoimmune diseases o to combat the pain which accompanies these diseases (S. Levin, *Isr. J. Med. Sci.* 19:955–958 (1983); K. Osther et al.. Proceedings of the Second International TNO Meeting on the Biology of the Interferon System, 18-22 Apr. 1983, in: The Biology of the Interferon System (1983) [Edward De Maeyer & Huub Schellekens, Eds.]Elsevier Science Publishers B.V., 527-533 (1983)).

In addition to these applications, it has been proposed that IFNγ be used in intracellular bacterial infections as well (A.F. Kiderlen et al., *Eur. J. Immunol.* 14:964-967 (1984); J. Mauel, Y. Buchmüller Rouiller, *Eur. J. Immunol.* 17:203-208 (1987)).

Furthermore, IFNγ has only been used to treat infections caused by parasitic protozoa (I.A. Clark et al., *J. Immunol.* 139:3493-3496 (1987); A.F. Kiderlen M.L. Lohmann-Matthes, Interdisciplinary conference on primary health care in the tropics, tropical diseases and zoonoses, 13.-15. Apr. 1987, Genf; S.G. Reed, *J. Immunol.* 140(12):4342-4347 (1988); Y. Suzuki et al., *Science* 240:516-518 (1988)). However, the effectiveness of this type of therapy was uncertain and in some cases even discouraging.

SUMMARY OF THE INVENTION

The aim of the present invention was therefore to prepare pharmaceutical compositions which, compared with the prior art, can be used effectively to treat parasitoses, advantageously to treat infections by endoparasites, particularly of the class Cestodes, preferably of the order Cyclophyllidea, more particularly of the genus Echinococcus, for example infections caused by *Echinoccocus multilocularis*.

The aim is achieved according to the invention by using a combination of IFNγ plus at least one anthelminthic to treat the above-mentioned parasitoses.

DETAILED DESCRIPTION OF THE INVENTION

Figures 2A, 2B, 2C:
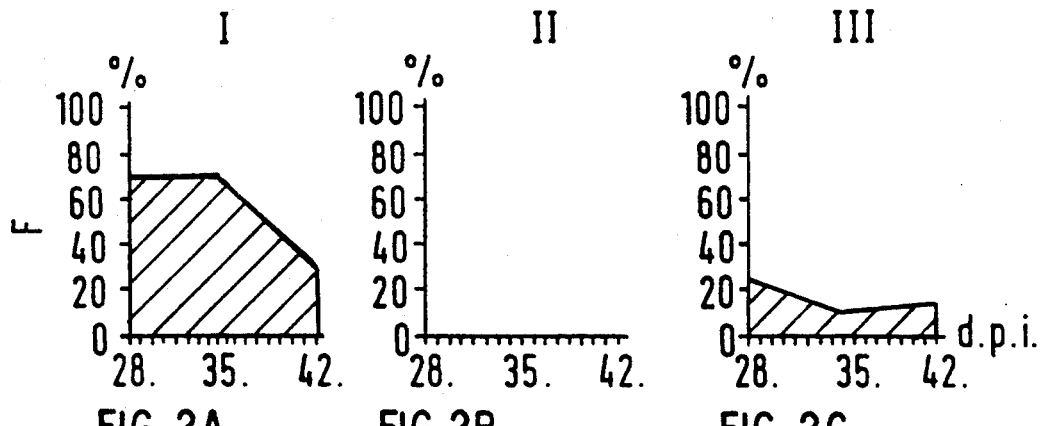
Figures 2D, 2E, 2F:
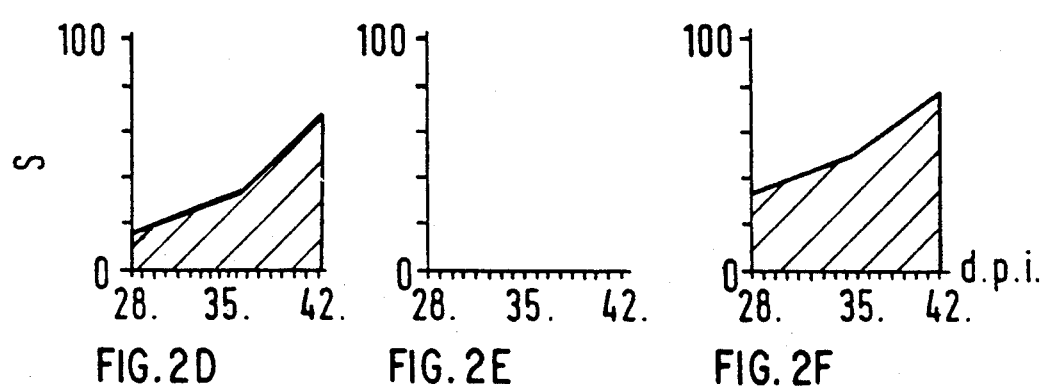
Figures 2G, 2H, 2I:
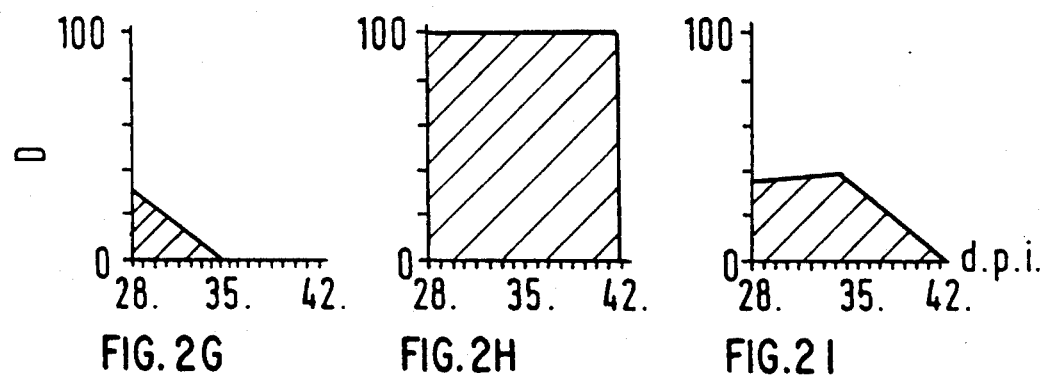
Figures 2J, 2K, 2L:
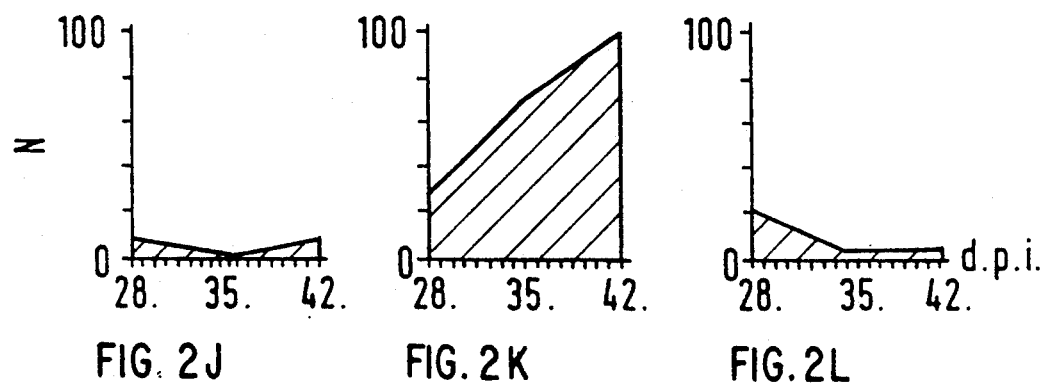

For the reasons stated above, it could not be expected that the administration of a combination of IFNγ and at least one anthelminthic according to the invention would represent an effective treatment against parasitoses.

Surprisingly, it was found in experiments on animals that the administration of a combination of IFNγ and at least one anthelminthic, the latter preferably selected from the group of chemically defined anthelminthics, in cases of one of the most dangerous parasitoses, with *Echinococcus multilocularis* the pathogen, would result in a higher level of degeneration or necrosis of the cysts than in treatment using mebendazole alone. The degree of degeneration of necrosis was total (100%) in some cases using the therapy according to the invention. Moreover, neither fertile nor sterile cysts could be found and accordingly only degenerate protoscoleces could be found.

In addition, in experimental oral infections of field mice (*Microtus arvalis*) which are a natural intermediate host, after the administration of a combination of IFNγ and the chemically defined anthelminthic mebendazole, a sharper distinction of the metacestode cysts could be observed in the liver compared with the surrounding liver tissue than after treatment with mebendazole alone.

In particular, the liver cells (hepatocytes) in the immediate vicinity of the focus of infection were less damaged than in treatment with mebendazole alone.

An experiment to see whether this also prevents or at least reduces the growth of buds from the germinative layer is currently in progress.

This surprising histological finding has additionally been confirmed by measuring the serum levels of the liver enzyme GPT (glutamate pyruvate transaminase). This enzyme occurs almost exclusively in the liver, where it is present only in the cytoplasm of the parenchyme cells.

The activity of GPT in the serum is increased depending on the degree of cell damage, owing to a different rate of release.

The normal value for GPT activity in the serum of field mice (*Microtus arvalis*) determined by the applicant's own investigations is on average 72 U/l. After oral infection with *Echinococcus multilocularis*, the GPT activity increased to 120 U/l on average 6 weeks after the infection.

By treatment with mebendazole alone over a period of 28 days the average GPT activity could only be reduced slightly to 107 U/l.

Surprisingly, it has now been found that by combining the four weeks mebendazole treatment over a period of 14 days with IFNγ, the GPT level in the serum was reduced to 78 U/l and is thus only slightly different from the normal value (72 U/l).

By contrast, monotherapy using mebendazole confirmed the exclusively parasitostatic activity of this chemotherapeutic agent. Admittedly, there was extensive damage to the cysts, protoscoleces and elements of the germinative layer, with symptoms of collapse and necrosis, but there were still buds present in the germinative layer. Positive reimplantation experiments support the finding that the parasite remains capable of regeneration.

Monotherapy with IFNγ showed a massive increase in the absolute weight of the cysts (LCM=larval cyst mass) up to 6 times the mass of untreated animals and is put down to the immunosuppressive properties of this cytotoxic substance. Histologically, the cysts were characterised by particularly frequent sterility, a thickened granulation wall and in some cases greater symptoms of degeneration. However, as a rule, a germinative layer as well as fertile cysts are present.

The multiple attack in the abdominal cavity, in some cases on the diaphragm as well, gives no indication of any inhibition of metastasis brought about by IFNγ.

The best results were achieved with the combined therapy using mebendazole and IFNγ. An LCM reduction rate of up to 99% was achieved.

As used herein, chemically defined anthelminthics is meant to include a chemical agent that is destructive to worms. Without intending to be limited, specific chemically defined anthelminthics, as described in *Remington's Pharmaceutical Sciences*, 16th edition (1980) pages 1179-1185, can include antimony potassium tartrate, areca, arecoline hydrobromide, bephenium hydroxynaphthoate, bithionol, carbon tetrachloride, chloroquine phosphate, diethylcarbamazine citrate, emetine hydrochloride, ethyl chloride, gentian violet, hexylresorcinol, hycanthone mesylate, iodoquinol, mebendazole, methylrosaniline chloride, metronidazole, niclosamide, niridazole, paromomycin, piperazine, piperazine citrate, piperazine phosphate, pyrantel pamoate, pyrvinium pamoate, quinacrine hydrochloride, stibocaptate, stibophen, suramin sodium, tetrachloroethylene, thiabendazole and thymol. The preferred chemically defined anthelminthics are benzimidazoles and the most preferred is mebendazole for use in this invention.

The IFNγ which is to be used for the combination according to the invention can be produced by the known methods of conventional cell cultures of animal or human origin, for example in accordance with W.R. Benjamin et al. *Proc. Natl. Acad. Sci. USA.* 79:5379-5383 (1982); Y.K. Yip et al., *Proc. Natl. Acad. Sci. USA* 78:1601-1605 (1981)a J.A. O'Malley, *Methods Enzymol.* 78:540-545 (1981); Y.K. Yip et al., *Proc. Natl. Acad. Sci. USA* 79:1820-1824 (1982), or using the equally well known technique of DNA recombination, for example according to P.W. Gray et al., *Nature* 295:503-508 (1982); E. Rinderknecht et al., *J. Biol. Chem.* 259:6790-6797; R. Devos et al., *Nucl. Acids Res.* 10:2487-2501 (1982).

Preferably the IFNγ used for the combination according to the invention is one which may be obtained by DNA recombination using the known methods.

It is known to the average person skilled in the art that natural allelic variations are individual-specific or species-specific and are manifested by one or more different amino acids or by different nucleotides or DNA sequences. Variations or mutations of this kind, which can also be produced by the known methods of DNA recombination or by controlled mutagenesis, as described for example by P.W. Gray et al.. (1982), loc. cit. and R. Devos et al.. (1982), loc. cit. include single or multiple substitutions, deletions, additions, insertions or inversions. Therefore, IFNγs of this kind are also included according to the invention.

For immunological reasons, the person skilled in the art knows that species-specific active substances are preferable when using biologically active substances native to the body. For the species-specific use of IFNγ according to the invention, therefore, it is preferable to use IFNγ isolated from the species-specific tissues in question or to use the nucleic acids (RNA, DNA) isolated from the species-specific tissues or cells to produce the IFNγ required by DNA recombination, but in particular it is preferred to use the polypeptide identical to the genuine IFNγ in question, having the known biological activity spectrum of IFNγ. Thus, for example, the IFNγ used on humans for the purposes of the invention will be a human IFNγ.

The IFNγ may be administered according to the invention by means of the pharmaceutical or galenic formulations which are known in the art and in common use for oral or parenteral administration, and preferably those used for parenteral administration, particularly for intravenous, intramuscular, subcutaneous, intracutaneous, intraarticular, intrathecal, intraperitoneal infusion or injection, including continuous infusions or intermittent infusions using the pumps available in the art.

For preparing a ready to use solution for the administration of IFNγ according to the invention, the person skilled in the art may use the aqueous infusible and injectable solutions known for this purpose, optionally together with the excipients, carriers and/or stabilisers known to him. A ready to use solution for the application according to the invention can be produced for example by dissolving highly purified IFNγ in "water for injection" or in phosphate-buffered physiological saline solution (pH 7 to 7.5) possibly with Tween and/or gelatine or human albumin as stabilisers, before use and then transferring the solution under sterile conditions into suitable containers (e.g. ampoules, bags). For the purpose of a simultaneous application of mebendazole and IFNγ it is possible to use liposomes producible e.g. according to EP-A213523.

The quantity of IFNγ to be administered for the purposes of the invention will depend on the dosages familiar to those skilled in the art, the gravity of the disease, the response rate and the progress of the disease as well as the side effects. In general, it can therefore be assumed that the dosage will have to be adjusted to suit individual criteria. One of skill in the art will be able to ascertain by routine screening or by routine testing the effective amount of IFN-γ needed to treat parasitoses in combination with at least one anthelminthic. For instance, the effective amount can be determined by serum levels of the liver enzyme GPT.

The anthelminthics to be used for the combination according to the invention, at least one of which is present as part of the combination according to the invention, are advantageously the known chemically defined anthelminthics, particularly those in the benzimidazole group, particularly mebendazole (methyl[5-benzoylbenzimidazole-2-carbamate)]. The substance mebendazole is known and is obtainable for example under the trade marks Vermox ® or Vermox ® forte (made by Janssen). The method of administration and dosage should be guided by the therapy schemes which are known for the above-mentioned anthelminthics.

The use of the combination of IFNγ and at least one anthelminthic according to the invention, advantageously IFNγ plus at least one anthelminthic selected from the group of chemically defined anthelminthics, particularly IFNγ plus at least one anthelminthic selected from the group of benzimidazoles, particularly IFNγ plus mebendazole, may either be administered by giving the two different types of active substance simultaneously or by giving them consecutively or sequentially by a suitable route. Advantageously, in the combined therapy according to the invention, first IFNγ and then one or more of the anthelminthics is administered.

LEGENDS RELATING TO THE FIGS.

FIG.1A-1L test unit A, gerbils; I=untreated, II=-mebendazole, III=mebendazole/IFNγ; F=fertility, S=sterility, D=degeneration, N=necrosis.

FIG. 2A-2L test unit B, gerbils; I =untreated, II =mebendazole, III=IFNγ; F, S, D and N as in FIG. 1.

Figure 3:
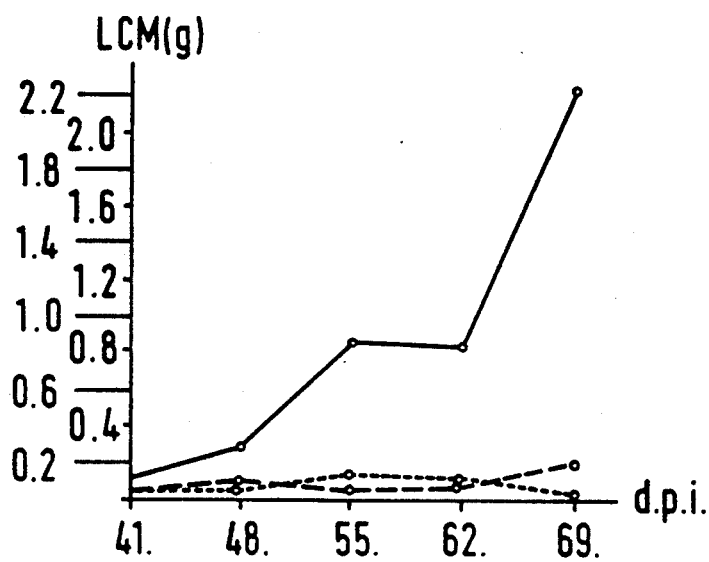

FIG. 3 change in the cyst weights (LCM) in test unit A, field mice; o—o=no therapy, o----o=mebendazole, o....o=mebendazole/IFNγ

FIG. 4A-4L test unit A, field mice; I=untreated, II=mebendazole, III - mebendazole/IFNγ; F, S, D and N as in FIG. 1.

Figure 5:
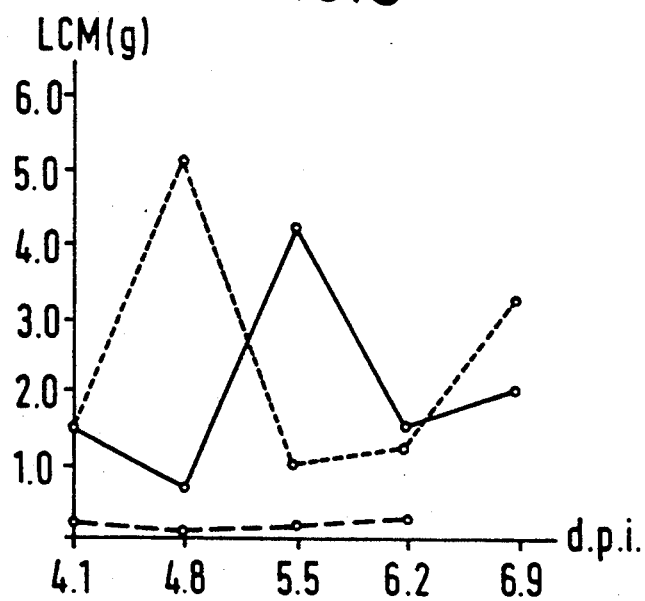

FIG. 5 change in the cyst weights (LCM) in test unit B, field mice; o—o=no therapy, o----o=mebendazole, o....o=IFNγ.

FIG. 6A-6L test unit B, field mice; I=untreated, II=mebendazole, III =IFNγ; F, S, D and N as in FIG. 1.

Examples are intended to illustrate the invention without restricting it in any way.

EXAMPLE 1

Findings and results in the qerbil Meriones unquiculatus as intermediate host.

The starting material used consisted of a total of 40 gerbils infected with metacestode material from *E. multilocularis,* these gerbils being subdivided into test units A and B as shown in Table 1.

TABLE 1

| | Test group | Type of therapy | Number of animals |
|---|---|---|---|
| Test unit A | I | none | 6 |
| n = 18 (8 male | II | mebendazole | 6 |
| 10 female) | III | mebendazole IFNγ* | 6 |
| Test unit B | I | none | 3 |
| n = 22 (15 male | II | mebendazole | 4 |
| 7 female) | III | IFNγ* | 15 |

*murine IFNγ produced by DNA recombination

The sex of the animals was selected at random and the age was between 2 and 4 months at the start of the experiment. The experimental animals were kept on sawdust and hay in makrolon cages in groups of 1 to 6, with a day/night cycle of 12 hours. Their standard diet was Altromin ® food (No. 1314) and they were given tap water ad libitum.

In order to infect animals, first of all field mice (*Microtus arvalis*) were infected by oral route with egg material taken from the intestines of a naturally infected fox. This infective material was then passed on vegetatively to Meriones unguiculatus, using the method of E. Hinz, *Tropenmed. Parasitol.* 23:387–390 (1972), after a 2 month interval, by administering 0.4 ml of a metacestode PBS (phosphate buffered solution) suspension to each experimental animal by intraperitoneal route (about 50% packaged material).

Mebendazole was administered by oral route by mixing ground up tablets (Vermox ® forte, made by Janssen, concentration of active substance 500 mg) to the food, which was also ground up, made into pellets using a laboratory press (L 175; Amandus Kahl Nachf.-/Reinbek) and made available to the animals ad libitum. In accordance with the experimental values obtained by J. Eckert et al., *Schweiz. med. Wschr.* 108:1104-1112 (1978), the dosage was 500 ppm, corresponding to a daily dose of about 30-50 mg/kg of body weight. Murine IFNγ produced by DNA recombination (Genentech Inc., South San Francisco, California, or prepared according to P.W. Gray, D.V. Goeddel, *Proc. Natl. Acad. Sci. USA* 80:5842–5846 (1983)) hereinafter referred to as IFNγ —was present in a sterile filtered solution (O.02M Tris, pH 7.5, 0.9% NaCl) with an IFNγ concentration of 1.1 mg/ml (specific activity: $1-2 \times 10^7$ U/mg of protein) and was diluted to 50 g/ml before administration with a 2% serum solution (gerbil serum/PBS). For each treatment 0.2 ml of this solution, corresponding to 10 g of IFNγ (specific activity: $1-2 \times 10^5$ U/mg of protein) were administered by intraperitoneal route.

The therapies (single substances and combination) began on the sixth day after the infection (d.p.i., dies oost infectionem).

Duration of therapy: mebendazole as a continuous therapy was given until the time of killing (test unit A by means of chloroform, test unit B by breaking the animals necks; 28th, 35th and 42nd d.p.i.), IFNγ was given every second day, 10 times in all.

The criteria used to assess the macroscopic-pathoanatomical findings were both the absolute cyst weight (LCM = larval cyst mass) relative to the time of killing and the location and constitution of the cyst conglomerates. In order to determine any reduction or increase in the absolute cyst weight of the two treated groups of test units A and B, the cyst weights of the untreated group were put at 100%.

Test unit A:

In the untreated gerbils, there was a constant sharp increase in the LCM as the infection went on.

In the group of animals treated with mebendazole, there was a sharp, slowly increasing reduction in the LCM, whilst the mebendazole/IFNγ-treated group exhibited a reduction which was initially somewhat higher and finally equal to that achieved with the mebendazole group.

The criteria used to assess the microscopic-pathohistological findings were the estimated percentage of fertile, sterile, degenerate and necrotised cysts observed in a histological section, the number and degree of maturity or vitality of the protoscolesces and cytohistopathological findings.

The percentages of fertility, sterility and degeneration together added up to 100%. Necrosis is part of degeneration but was shown separately in the interests of clarity.

The untreated animals showed a reduction in fertile cysts from the 28th d.p.i. to the 42nd d.p.i. from 60% to 25%. By contrast, the sterility of the cysts increased, with a maximum of 50% on 35th d.p.i. On the other hand, the proportion of degenerate cysts was smaller (maximum 30% on 42nd d.p.i.), with no sign of any necrotic decomposition.

The animals treated with mebendazole showed no fertile cysts at all and only a few sterile cysts (maximum of 25% on 35th d.p.i.). By contrast, the proportion of degenerate cysts was very high (maximum of 100% on 28th and 42nd d.p.i.). In some places the necrotic decomposition reached a maximum of 60% on 35th d.p.i. The beginnings of lytic processes from the centre of the cyst complex outwards were observed in some parts.

The animals treated with mebendazole/IFNγ had neither fertile nor sterile cyst material. Degeneration remained constant at 100%, with a sharply decreasing necrotic component, from 80% on 28th d.p.i. to 25% on 42nd d.p.i. Here the necrosis was basically accompanied by lytic decomposition in the centre of the cyst complex (FIG. 1).

In the untreated group there were a few mainly mediummature, fewer young and mature protoscoleces. Young means the beginning of a head but still with an internal cavity, medium mature means still without suction pads and ring of hooks and mature means with suction pads and ring of hooks. On 28th and 42nd d.p.i., however, a few degenerate scoleces were observed, which were recognisable by their amorphous cell contents.

Both the mebendazole groups and the groups treated with mebendazole/IFNγ showed only a few, exclusively degenerate protoscoleces.

Test unit B:

In the untreated gerbils, as the infection went on, there was first a slight increase and then a slight drop in the cyst weight.

The mebendazole group showed a slightly smaller reduction in the LCM than the same group of test unit A but was fundamentally comparable. The IFNγ group first of all showed a reduction in the LCM of about ⅓ compared with the untreated control animal but then, totally unexpectedly, showed a sharp approximately 6-fold increase.

In terms of their fertility, sterility, degeneration and necrosis, the untreated animals tended to correspond to those of test unit A. Only a slight necrotic decomposition was observed.

In the animals treated with mebendazole, in contrast to test unit A, there were no fertile or sterile cysts. The degree of degeneration was 100%, with a sharply increasing proportion of necrosis.

The animals treated with IFNγ showed only low-level fertile cysts, with a maximum of 25% on the 28th d.p.i. The degree of sterility on the other hand increased rapidly (maximum 80% on 42nd d.p.i.). Degeneration on the other hand fell from just 40% to 5%. The proportion of necrosis was small (FIG. 2).

Regarding the total number, degree of maturity or vitality of the protoscoleces, in the untreated group there were some protoscoleces of which some were young and some medium mature but few were mature. No degenerate head parts were found.

The mebendazole group also contained some protoscoleces, but these were all degenerate.

In the IFNγ group, at the 28 day stage, only a few young to medium mature and degenerate protoscoleces were found. At the 35 day stage the number of heads had been reduced still further. There were only medium mature to mature protoscoleces but only in one case were there any degenerate protoscoleces. At the 42 day stage there were few which ranged from young to mature, but no degenerate scolex structures.

EXAMPLE 2

Findings and results using the field mouse *Microtus arvalis* as intermediate host.

The test material used consisted of a total of 56 field mice infected with metacestode material from *E. multilocularis*. The metacestode material was vegetatively passed on after the oral primary infection using the method of E. Hinz, *Trooenmed. Parasitol.* 23:387–390 (1972). Analogously to Example 1, the animals were divided into two test units A and B (Table 2).

TABLE 2

|  | Test group | Mode of treatment | Number of animals |
| --- | --- | --- | --- |
| Test unit A | I | none | 10 |
| n = 30 (17 male, | II | mebendazole | 10 |
| 13 female) | III | mebendazole plus IFNγ* | 10 |
| Test unit B | I | none | 5 |
| n = 26 (9 male, | II | mebendazole | 4 |
| 17 female) | III | IFNγ* | 17 |

*murine IFNγ prepared by DNA recombination

The selection of the sex, the age of the animals, the method of keeping the animals, feeding them, administering the metacestode suspension for the vegetative passing on, the infective dose and the mode of administering the mebendazole were as specified in Example 1. The IFNγ solution was administered analogously to Example 1, except that field mouse serum/PBS was used for dilution and for each treatment 0.1 ml of the finished solution, corresponding to 5 g of IFNγ (specific activity $0.5-1 \times 10^5$ U/mg of protein) was administered.

The treatments (single substances and combinations) started on 21st d.p.i. This delayed start of the therapy compared with Example 1 is due to the slower growth of the metacestode material in *Microtus arvalis* as a natural intermediate host.

Duration of treatment: mebendazole has a continuous treatment up to the time of killing (test unit A using chloroform, test unit B by breaking the animals necks; 41st, 48th, 55th, 62nd and 69th d.p.i.), IFNγ as specified in Example 1.

For the reimplantation tests, in 2 field mice (one treated with mebendazole alone) the other treated with mebendazole and IFNγ combined, when the section is taken on the 62nd d.p.i. an additional piece of cyst is isolated, placed in PBS antibiotic solution and cooled overnight. After the piece of cyst had been divided into two substantially equal parts, they were reimplanted into two male gerbils using the method of E. Grimminger, Thesis, University of Hohenheim (1984). The assessment criteria for the macroscopicpathoanatomical findings have already been mentioned in Example 1.

TEST UNIT A:

The weights of the cysts from the untreated field mice increased stepwise, compared with the gerbils, with a plateau apparently being reached between the 55th and 62nd d.p.i., after which the weights rapidly shot up again. By comparison, in the animals treated with mebendazole, there was first of all a slight increase in the LCM, followed by a relatively sharp reduction, peaking on the 55th d.p.i. and falling slightly again towards the 69th d.p.i. The field mice treated with mebendazole and IFNγ combined showed a reduction of about ¾ compared with the untreated animals on 41st d.p.i., which developed constantly up to a maximum of 99% on the 69th d.p.i. (FIG. 3).

The cysts from all 3 test groups were generally distributed over the entire abdominal cavity, with the exception of the pleural cavity. In 3 cases, in the untreated group, there were cysts which had grown with the internal lining of the abdomen.

In the group treated with mebendazole and IFNγ combined, no attack on the liver could be found, by contrast with the other two test groups.

With regard to fertility, sterility, degeneration and necrosis, the level of fertility in the untreated group was 100% on the 41st and 69th d.p.i. and this fell by barely 20% in between. The sterility and degeneration levels were correspondingly low.

The group treated with mebendazole showed no fertility of any kind and only 15% sterility on the 41st d.p.i. Degeneration was correspondingly high, with a virtually identical proportion of necrosis.

In the group treated with mebendazole and IFNγ, no fertile or sterile cysts could be detected. Degeneration and necrosis were constant at 100% (FIG. 4).

Regarding the total number, maturity or vitality of the protoscoleces, the untreated animals continuously exhibited numerous, usually mature head structures, only a few of them being young or medium mature and seldom degenerate.

In the animals treated with mebendazole and mebendazole/IFNγ, on the other hand, only individual protoscoleces appeared, all of which were degenerate.

Test unit B p The untreated group showed a gently rising, zigzag shaped pattern for the weights of the cysts, peaking on 55th d.p.i.

The group treated with mebendazole showed a relatively sharp reduction in the LCM with a peak on the 55th d.p.i. The group treated with IFNγ, on the other hand, exhibited a completely conceptless image. The zigzag configuration was similar to that of the untreated group, but the LCM maximum was shifted forward to the 48th d.p.i. Analogously to Example 1, there is initially a massive increase in the LCM (about a 6-fold increase) under IFNγ therapy, which then falls drastically again and does not begin to increase sharply again until the 69th d.p.i. (FIG. 5).

With regard to fertility, sterility, degeneration and necrosis, the maximum level of fertility in the untreated group was reached on 48th and 55th d.p.i. with 90%. A fall to only 30% fertility occurred on 62nd d.p.i. but on 69th d.p.i. this had risen again to 70% fertility. Sterility hardly ever occurred, whereas degeneration or necrosis (in this case occurring to an identical extent, i.e. the degenerate tissue is totally necrotised) proceeded negatively in synchronism with the level of fertility.

The group treated with mebendazole were characterised exclusively by a 100% degeneration or necrosis (again overlapping entirely).

Finally the IFNγ-treated group exhibited a moderate fertility of between 30 and 60%. The degree of fertility reached its peak on 48th d.p.i. at just 40% and then fell to below 10%. Degeneration and necrosis (again overlapping completely) increased sharply from 48th to 55th d.p.i. from a good 20% to 65% and fell back to 30% by 69th d.p.i. (FIG. 6).

Regarding the total number, degree of maturity or vitality of the protoscoleces, the untreated animals exhibited from a few to a large number of usually mature, sometimes young or moderately mature, but also degenerate protoscoleces.

In the animals treated with mebendazole, there were a few head structures, but these were degenerate. The animals treated with IFNγ exhibited, by the 55th d.p.i., a few usually young or mature, occasionally medium-mature and now and then a few degenerate protoscoleces, on average. From the 62nd d.p.i., a large number of protoscoleces appeared, most of them mature, some of them young and fewer still medium-mature and in some cases degenerate.

What is claimed is:

1. A pharmaceutical composition for the treatment of parasitoses comprising an active substance combination of interferon-gamma (IFN-γ) and at least one anthelminthic.

2. The pharmaceutical composition according to claim 1, characterised in that said anthelminthic is selected from the group of chemically defined anthelminthics.

3. The pharmaceut according to claim 2, characterised in that said anthelminthic is selected from the group of benzimidazoles.

4. The pharmaceutical composition according to claim 3, characterised in that said anthelminthic is mebendazole.

5. The pharmaceutical composition according to one of claims 1 to 4, characterised in that said IFNγ is species-specific and originates from natural cells or has been prepared by DNA recombination.

6. A method for treating infections caused by endoparasites in mammals comprising administering a therapeutically effective amount of the pharmaceutical composition of claim 1.

7. The method of claim 6 wherein the infection treated is caused by cestodes.

8. The method of claim 7 wherein the infection treated in caused by *Echinococcus multilocularis*.

* * * * *